United States Patent [19]

Kartinos

[11] 4,336,157
[45] Jun. 22, 1982

[54] PROCESS FOR RECLAIMING BILIVERDIN-CONTAINING FLUIDS

[75] Inventor: Nicholas J. Kartinos, Park Ridge, Ill.

[73] Assignee: Baxter Travenol Laboratories, Inc., Deerfield, Ill.

[21] Appl. No.: 163,857

[22] Filed: Jun. 27, 1980

[51] Int. Cl.³ .................... G01N 33/48; G01N 31/16
[52] U.S. Cl. ............................... 252/408; 23/230 B; 23/905; 210/749
[58] Field of Search ............ 252/408; 23/230 B, 905; 210/59

[56] References Cited

U.S. PATENT DOCUMENTS

| | | | |
|---|---|---|---|
| 3,492,095 | 1/1970 | Tillem | 252/408 |
| 3,652,222 | 3/1972 | Dennet et al. | 252/408 |
| 3,873,269 | 3/1975 | Kraffczyk et al. | 252/408 |
| 3,918,905 | 11/1975 | Warrem et al. | 252/408 |
| 4,001,200 | 1/1977 | Bonsen | 252/408 |
| 4,201,694 | 5/1980 | Louderback | 252/408 |
| 4,288,343 | 9/1981 | Louderback | 252/408 |
| 4,311,665 | 1/1982 | Wu | 252/408 |

OTHER PUBLICATIONS

Michaelsson, M., Scand. J. Clin. Lab. Invest., Suppl. 56, vol. 13, pp. 1–80, (1961).

*Primary Examiner*—Teddy S. Gron
*Attorney, Agent, or Firm*—Max D. Hensley; Paul C. Flattery; Lawrence W. Flynn

[57] ABSTRACT

The green shade imparted to serum or plasma by biliverdin is eliminated by contacting the contaminated fluid with dithionite ion.

10 Claims, No Drawings

PROCESS FOR RECLAIMING BILIVERDIN-CONTAINING FLUIDS

BACKGROUND OF THE INVENTION

This invention relates to the processing of bilirubin-containing substances such as plasma and serum. In particular, it is concerned with reclaiming plasma or serum which has become green in color due to bilirubin oxidation as well as maintaining the proper color after reclamation and during storage or processing. The term "reclamation" means elimination of the biliverdin pigment in the fluid, ordinarily by converting biliverdin to a substance having an adsorption spectrum similar or identical to that of bilirubin. The primary focus of the invention is upon the manufacture and stabilization of serum intended for use as controls, calibrators or standards in analytical methods.

Bilirubin is a bile pigment structurally related to hematoporphyrin and hematin. It forms complexes with proteins such as albumin found in serum and contributes to the characteristic straw yellow color or normal plasma or serum. Exposure of plasma or serum to oxygen under certain conditions can result in the oxidation of bilirubin to biliverdin, along with a concomitant color change from yellow to green. This problem is particularly acute with out dated plasma and serum derived therefrom by defibrination. This serum is unmarketable for use in clinical laboratories because of its objectional color.

U.S. Pat. No. 4,201,694 discloses increasing the shelf-life of a serum bilirubin reference composition by adjusting the serum pH to between about 8.3 and 9.5 and providing a sulfhydryl compound to further enhance the bilirubin stability.

OBJECTS OF THE INVENTION

It is an object of this invention to reclaim biliverdin-contaminated body fluids without adversely affecting the activity of other serum constituents.

A specific object is reclaiming such fluid without resorting to deleterious alkaline pH levels.

A further object is reclaiming such fluid by use of a reagent which can be readily treated so as to not leave a residue capable of interfering with the subsequent use of the fluid as a control, calibrator or standard.

An additional object is to provide a reagent for reclaiming the fluid which will leave a residual substance capable of inhibiting the reoxidation of bilirubin to biliverdin.

SUMMARY OF THE INVENTION

The above objects are achieved by a method which comprises contacting a biliverdin-containing substance with dithionite ions. Contacting the biliverdin with dithionite is believed to reduce the biliverdin to bilirubin while simultaneously yielding a mixture of bisulfite, sulfate and hydrogen ions. The bisulfite residue is effective in stabilizing the bilirubin against oxidation during storage or by processing steps which increase the oxygen tension of the solution, e.g., pressurized filtration. The dithionite is especially advantageous because it rapidly converts green plasma or serum to a straw yellow color without the need to resort to alkaline pH. It was most surprising that dithionite was effective in this manner because other reducing agents such as ascorbic acid, hydroxylamine-HCl, N-acetyl cysteine and sodium bisulfite were unsatisfactory in reclaiming green serum. Further, it was not necessary to add a metal-complexing agent such as ethylenediamine tetraacetic acid to achieve the desired results.

The nature of the biliverdin-containing substances which may be reduced by the process of this invention is not critical. Essentially any biliverdin-contaminated aqueous solution can be successfully treated, whether or not the biliverdin is bound by protein or is in a body fluid. The solution may contain reducible compounds other than biliverdin, e.g., proteins containing disulfide bonds. Since bilirubin oxidation is a problem most often faced with plasma or serum, particularly out-dated anticoagulated plasma, plasma and serum are preferred for treatment according to this invention. The plasma or serum may be from frozen pools or lyophilized material that has developed biliverdin content during storage or lyophilization.

The dithionite, also known as hydrosulfite, may be mixed with the biliverdin solution as a dry powder to avoid increasing the water content of the solution. However, it is preferred to add the dithionite as an aqueous solution when treating protein-containing solutions; this minimizes the probability of creating high dithionite concentrations in transient, localized portions of the solutions where solid dithionite is dissolving. Solutions of about from 5% to 25% by weight of dithionite are typical, with about 10% being preferred.

The dithionite salt which is used is not critical. The amount of dithionite needed to convert the biliverdin content of a typical green serum pool is so small that ordinarily the contributed cation will not raise the physiological concentration of that cation in serum outside of the normal range. Thus, the alkali metal salts, preferably sodium, may be employed. Should it be desired to not elevate the content of cation analytes, quaternary ammonium salts such as tetramethylammonium dithionite or others described in U.S. Pat. No. 4,141,856 may be useful.

The amount of dithionite to be used is an amount sufficient to reduce the biliverdin content of the aqueous solution treated to a level at which the characteristic color biliverdin is not visible. It is not necessary to completely reduce all of the biliverdin in solution if other pigments make this unnecessary from a visual standpoint. About from 0.1 to 0.5 g of dithionite/liter of serum is typically effective with serum or plasma; about 0.3 is preferred. The proper amount of dithionite will therefore depend upon the level of contamination of biliverdin, the presence or absence of other pigments and the concentration of substances which may compete with biliverdin for reduction by dithionite. Simply titering dithionite into the solution until the biliverdin color disappears is the most satisfactory technique for establishing the proper quantity of dithionite to be used.

A significant advantage of dithionite in reclaiming biliverdin-contaminated fluids is that it is effective at pH levels less than 8.3. Hence the pH of the starting, biliverdin-containing solution may be as low as about 5.0, although extreme pH may adversely affect labile constituents in biologicals such as serum. For example, acid phosphatase is inactivated at a pH above about 8.0. Thus, it is generally preferred to maintain the pH at about from 6.5 to 8.0, preferably about 7.0, during the addition of dithionite.

After the biliverdin reduction has been completed to the desired degree the pH should be adjusted to at least about 6.5 if it has not been maintained previously above that level. The bisulfite residue remaining after the reaction of dithionite is optimally effective in preventing reoxidation of bilirubin, at neutral or alkaline pH. The residual bisulfite ion at a pH of about from 6.5 to 8.0 will stabilize the bilirubin content of serum or plasma under further processing steps during which bilirubin is susceptible to oxidation, e.g. ultrafiltration, dialysis, or pressurized sterile filtration.

It is generally preferred to remove residual bisulfite and other by-products from serum or plasma which is intended for use as controls or standards in clinical laboratories. Hyposulfite and bisulfite, to a lesser degree, interfere in redox assays for bilirubin and other analytes. It is convenient to remove both substances during the ultrafiltration or dialysis steps that are otherwise conventional in the manufacture of controls from plasma. Dithionite and bisulfite pass through the ultrafiltration or dialysis membranes along with salts and other low molecular weight compounds that are present in excess in such plasma. Other methods, e.g., oxidation of the bisulfite to sulfate, will be apparent to the skilled artisan. However, it is by no means essential that the residual dithionite and bisulfite be removed if the product is not to be employed in assays which are based on a change in redox potential brought on by an analyte. The serum or plasma may then be treated in conventional fashion, e.g., addition of analytes to the ultrafiltrate, followed by lyophilization The invention will be more fully understood in view of the following examples.

EXAMPLE 1

Control serum reconstituted from a lyophilized pool was found to be forest green in color. Sodium dithionite as a 10% solution in water was added to 500 ml of the control serum with stirring, during which the serum was protected from light with aluminum foil. When approximately 1.6 ml of 10% sodium dithionite solution had been added the color reverted from forest green to a dark straw yellow. The pH stayed at approximately 6.7 during the process.

EXAMPLE 2

Green serum obtained by defibrination of outdated citrate-phosphate-dextrose plasma was employed in this experiment. Approximately 1 ml of 10% sodium dithionite solution was required to convert the color from pale green to mustard yellow. The pH prior to and after treatment was about 5.6.

EXAMPLE 3

Paired aliquots of two lots of pooled serum were adjusted pH 6.8 and 7.5, sodium dithionite added to yield a calculated concentration of 2 mM and each aliquot maintained at 37° C. for 24 hours. The normal serum color was retained throughout the incubation with dithionite at both pH levels. The controls without dithionite were both green, although those at pH 7.5 were less so than at 6.8.

EXAMPLE 4

This example demonstrates that dithionite and its reaction products with serum which interfere in subsequent bilirubin assays can be removed by ultrafiltration. Sodium dithionite was added to a green serum sample until the color changed to yellow (about 2 mM calculated concentration), the pH adjusted to 7.2, the serum ultrafiltered with an AMF Cuno 60 ultrafiltration cartridge until the volume was reduced about 25%, water added to regain the original volume and the serum then sterile filtered through a 0.3 micron membrane. The bilirubin concentration as determined on the DuPont ACA system was 2.50 mg/dl before dithionite treatment, 0.99 mg/dl before ultrafiltration and 2.32 mg/dl after ultrafiltration and sterile filtration. The minor discrepancy between the starting and final bilirubin assayed concentration was not attributed to the presence of residual interfering materials but rather to the loss of free sample bilirubin during ultrafiltration.

I claim:

1. The method comprising contacting a biliverdin-containing substance with dithionite ions.

2. The method of claim 1 wherein the substance is plasma or serum.

3. The method of claim 2 wherein the dithionite ions are contacted with the plasma or serum by adding an aqueous solution containing about from 5% to 25% by weight of dithionite.

4. The method of claim 2 wherein the plasma or serum is contacted with sufficient dithionite to yield a hyposulfite concentration of about from 0.1 to 0.5 g of dithionite/liter.

5. The method of claim 2 wherein the pH of the plasma or serum is less than 8.3.

6. The method of claim 5 wherein the pH is between about 6.8 and about 8.0.

7. The method of claim 2 wherein sufficient dithionite is added to change the plasma or serum from green to yellow.

8. The method of claim 7 wherein dithionite and bisulfite are removed from the plasma or serum after the color change from green to yellow.

9. The plasma or serum made by the process of claim 7 which contains residual bisulfite ions.

10. A method for reclaiming serum or plasma having a green color due to the presence of biliverdin, comprising titering dithionite into the serum or plasma until the plasma or serum exhibits a yellow color, followed by ultrafiltration or dialysis of the plasma or serum.

* * * * *